(12) United States Patent
Hashiba et al.

(10) Patent No.: US 9,598,779 B2
(45) Date of Patent: *Mar. 21, 2017

(54) METHOD FOR REDUCING CARBON DIOXIDE

(71) Applicant: Panasonic Intellectual Property Management Co., Ltd., Osaka (JP)

(72) Inventors: Hiroshi Hashiba, Osaka (JP); Masahiro Deguchi, Osaka (JP); Satoshi Yotsuhashi, Osaka (JP); Yuka Yamada, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/935,370

(22) Filed: Nov. 6, 2015

(65) Prior Publication Data
US 2016/0060770 A1  Mar. 3, 2016

Related U.S. Application Data

(63) Continuation of application No. PCT/JP2014/003185, filed on Jun. 16, 2014.

(30) Foreign Application Priority Data

Jul. 5, 2013  (JP) .................................. 2013-141473

(51) Int. Cl.
*C25B 1/00* (2006.01)
*C01B 31/18* (2006.01)
(Continued)

(52) U.S. Cl.
CPC .............. *C25B 1/003* (2013.01); *C01B 31/18* (2013.01); *C07C 51/00* (2013.01); *C25B 3/04* (2013.01);
(Continued)

(58) Field of Classification Search
CPC .. C25B 3/04; C25B 1/003; C25B 9/08; C25B 11/0442; C25B 11/0447; B01J 35/004; C07C 51/00; C01B 31/18
(Continued)

(56) References Cited

U.S. PATENT DOCUMENTS 8,696,883 B2 * 4/2014 Yotsuhashi ............. C25B 1/003
205/340
8,709,227 B2 * 4/2014 Deguchi ................. C25B 1/003
205/340
(Continued)

FOREIGN PATENT DOCUMENTS

JP  4-166076  6/1992
JP  5-311476  11/1993
(Continued)

OTHER PUBLICATIONS

International Search Report of PCT application No. PCT/JP2014/003185 dated Aug. 26, 2014.
(Continued)

*Primary Examiner* — Keith Hendricks
*Assistant Examiner* — Colleen M Raphael
(74) *Attorney, Agent, or Firm* — McDermott Will & Emery LLP

(57) ABSTRACT

In a carbon dioxide reduction method according to the present disclose, used is a carbon dioxide reduction device comprising a cathode container in which a first electrolyte containing carbon dioxide is stored, an anode container in which a second electrolyte is stored, a solid electrolyte membrane, a condenser, a cathode electrode having a metal or a metal compound on the surface thereof, and anode electrode having a region formed of a nitride semiconductor layer in which a GaN layer and an $Al_xGa_{1-x}N$ layer are stacked. The anode electrode is irradiated with light con-
(Continued)

densed by the condenser and having a wavelength of not more than 360 nanometers to reduce the carbon dioxide contained in the first electrolyte on the cathode electrode.

12 Claims, 4 Drawing Sheets

(51) Int. Cl.
 *C07C 51/00* (2006.01)
 *C25B 3/04* (2006.01)
 *C25B 9/08* (2006.01)
 *C25B 11/04* (2006.01)
(52) U.S. Cl.
 CPC ............ *C25B 9/08* (2013.01); *C25B 11/0442* (2013.01); *C25B 11/0447* (2013.01)
(58) Field of Classification Search
 USPC ........................................................ 205/340
 See application file for complete search history.

(56) References Cited

U.S. PATENT DOCUMENTS

| | | | | |
|---|---|---|---|---|
| 9,157,158 | B2* | 10/2015 | Deguchi | C25B 1/003 |
| 2005/0178427 | A1 | 8/2005 | Kelly et al. | |
| 2010/0133110 | A1* | 6/2010 | Nocera | C25B 1/003 |
| | | | | 205/340 |
| 2010/0133111 | A1 | 6/2010 | Nocera et al. | |
| 2013/0118907 | A1 | 5/2013 | Deguchi et al. | |
| 2014/0346053 | A1* | 11/2014 | Deguchi | C25B 1/003 |
| | | | | 205/340 |
| 2014/0360883 | A1* | 12/2014 | Deguchi | C25B 1/003 |
| | | | | 205/340 |
| 2015/0182937 | A1* | 7/2015 | Futakuchi | B01J 19/127 |
| | | | | 422/82.02 |
| 2015/0218719 | A1* | 8/2015 | Deguchi | C25B 1/003 |
| | | | | 205/340 |
| 2016/0222525 | A1* | 8/2016 | Noda | C25B 1/10 |
| | | | | 205/340 |

FOREIGN PATENT DOCUMENTS

| | | |
|---|---|---|
| JP | 7-188961 | 7/1995 |
| JP | 2001-089887 | 4/2001 |
| JP | 2003-069070 | 3/2003 |
| JP | 2003-275599 | 9/2003 |
| JP | 2007-526948 | 9/2007 |
| JP | 2012-036414 | 2/2012 |
| JP | 2012-505310 | 3/2012 |
| JP | 2013-017929 | 1/2013 |
| WO | 2012/046374 | 4/2012 |
| WO | 2013/031063 | 3/2013 |

OTHER PUBLICATIONS

Yoshio Hori, "Utilization of Carbon Dioxide by Electrolytic Reduction", Journal of Fiber Science and Technology, vol. 48, No. 1, 1992, pp. 38-42.

* cited by examiner

METHOD FOR REDUCING CARBON DIOXIDE

CROSS-REFERENCE TO RELATED APPLICATION

This is a continuation of International Application No. PCT/JP2014/003185, with an international filing date of Jun. 16, 2014, which claims priority of Japanese Patent Application No. 2013-141473, filed on Jul. 5, 2013, the contents of which are hereby incorporated by reference.

BACKGROUND

1. Technical Field

The present disclosure relates to a method for reducing carbon dioxide using light energy.

2. Description of the Related Art

PTL1-PTL 3 disclose a method for reducing carbon dioxide using light energy.

PTL 4 discloses a photosynthesis reactor system in which sunlight is condensed and which causes a microorganism to perform photosynthesis.

PTL 5 and PTL 6 disclose a structure in which sunlight is condensed using a lens or a mirror in a device for reducing carbon dioxide using light energy.

PTL 7 discloses an anode electrode used for a device for reducing carbon dioxide using light energy. The anode electrode has a region formed of a nitride semiconductor layer in which a GaN layer and an $Al_xGa_{1-x}N$ layer ($0<x\leq1$) are stacked.

CITATION LIST

Patent Literatures

PTL 1: Japanese Patent Application laid-open Publication No. Hei 05-311476

PTL 2: Japanese Patent Application laid-open Publication No. Hei 07-188961

PTL 3: WO 2012/046374

PTL 4: Japanese Patent Application laid-open Publication No. Hei 04-166076

PTL 5: Japanese Patent Application laid-open Publication No. 2003-275599

PTL 6: Japanese Patent Application laid-open Publication No. 2013-017929

PTL 7: Japanese Patent Publication No. 5236125

SUMMARY

The present invention provides a method for reducing carbon dioxide using a carbon dioxide reduction device, the method comprising:

(a) preparing the carbon dioxide reduction device comprising:
  a cathode container;
  an anode container;
  a solid electrolyte membrane;
  a condenser;
  a cathode electrode; and
  an anode electrode, wherein
  the cathode electrode comprises a metal or a metal compound on a surface thereof;
  the anode electrode comprises, on a surface thereof, a region formed of a nitride semiconductor layer in which a GaN layer and an $Al_xGa_{1-x}N$ layer ($0<x\leq1$) are stacked;
  a first electrolyte is stored in the cathode container;
  a second electrolyte is stored in the anode container;
  the cathode electrode is in contact with the first electrolyte;
  the anode electrode is in contact with the second electrolyte;
  the solid electrolyte membrane is interposed between the cathode container and the anode container;
  the first electrolyte contains carbon dioxide; and
  the cathode electrode is electrically connected to the anode electrode without an external power supply; and (b) irradiating the anode electrode with light condensed through the condenser and having a wavelength of not more than 360 nanometers to reduce the carbon dioxide contained in the first electrolyte on the cathode electrode.

The present invention provides a novel carbon dioxide reduction method in which reduction efficiency of carbon dioxide is improved.

DETAILED DESCRIPTION OF THE EMBODIMENT

Figure 1:
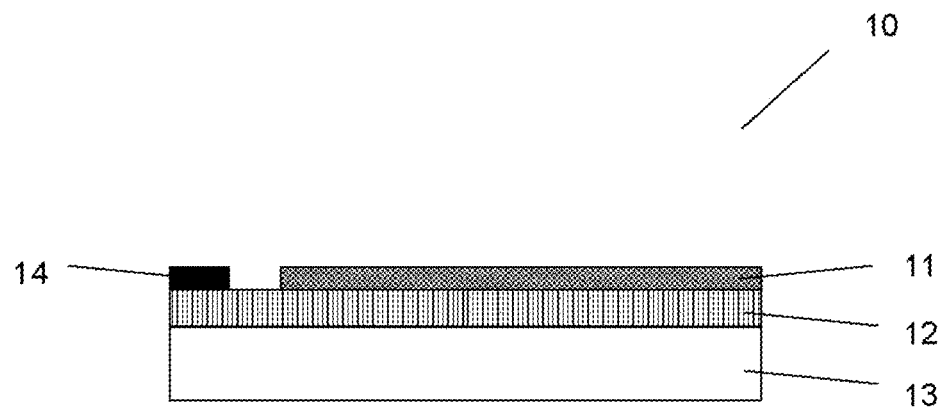
FIG. 1 is a cross-sectional view of an anode electrode according to the present disclosure.

Underlying Knowledge Forming Basis of the Present Disclosure

Underlying knowledge forming basis of the present disclosure will be described below.

PTL 2 discloses that an anode electrode is irradiated with light to reduce carbon dioxide contained in an electrolyte on a cathode electrode. In particular, the anode electrode is irradiated with light to generate carriers (i.e., electrons and holes) on the anode electrode. Then, the electrons generated on the anode electrode migrate to the cathode electrode through a conducting wire. On the cathode electrode, carbon dioxide contained in the electrolyte is reduced with the electrons which have migrated from the anode electrode and a reduction product is produced.

The production amount of the reduction product of carbon dioxide generated on the cathode electrode is dependent on the amount of the electrons generated on the anode electrode. In other words, it is expected that the production amount of the reduction product of the carbon dioxide generated on the cathode electrode is constant, if the amount of the electrons generated on the anode electrode by irradiating the anode electrode with the light is constant.

However, the present inventors considered this matter aggressively. As a result, the present inventors found the following fact and invented a carbon dioxide reduction method using a carbon dioxide reduction device according to the present disclosure.

In order to increase the intensity of the light with which the anode electrode is irradiated, the present inventors provide the carbon dioxide reduction device disclosed in PTL 2 with a light condensing member (hereinafter, referred to as "condenser"). Using the condenser, light emitted from a light source is condensed and the anode electrode is irradiated with the condensed light. The position, the light intensity, and the irradiation area of the condenser are adjusted so that the energy amount which the anode electrode obtains from the light source is constant. As a result, the present inventors confirmed that the light intensity per unit area is increased to increase the production amount of the reduction product of carbon dioxide generated on the cathode electrode. In other words, the present inventors found through the experiment results that the production amount of the reduction product of carbon dioxide generated on the cathode electrode is increased although the amount of the electrons generated on the anode electrode is constant, since the energy amount which the anode electrode obtains from the light source is constant.

The present disclosure is based on the above-mentioned findings.

A method for reducing carbon dioxide according to a first aspect of the present disclosure is a method for reducing carbon dioxide using a carbon dioxide reduction device. The method comprises steps (a) and (b). In the step (a), prepared is the carbon dioxide reduction device comprising a cathode container, an anode container, a solid electrolyte membrane, a condenser, a cathode electrode, and an anode electrode. The cathode electrode comprises a metal or a metal compound on a surface thereof. The anode electrode comprises, on a surface thereof, a region formed of a nitride semiconductor layer in which a GaN layer and an $Al_xGa_{1-x}N$ layer ($0<x\le1$) are stacked. A first electrolyte is stored in the cathode container. A second electrolyte is stored in the anode container. The cathode electrode is in contact with the first electrolyte. The anode electrode is in contact with the second electrolyte. The solid electrolyte membrane is interposed between the cathode container and the anode container. The first electrolyte contains carbon dioxide. The cathode electrode is electrically connected to the anode electrode without an external power supply. In the step (b), the anode electrode is irradiated with light condensed through the condenser and having a wavelength of not more than 360 nanometers to reduce the carbon dioxide contained in the first electrolyte on the cathode electrode.

According to the first aspect, carbon dioxide reduction reaction on the cathode electrode is promoted by irradiating the anode electrode with the light condensed using the condenser. In other words, the production amount of the reduction product of carbon dioxide is increased.

In the method for reducing carbon dioxide according to a second aspect of the present disclosure, the light having a wavelength of not more than 360 nanometers may be condensed using the condenser in the step (b) included in the first aspect, and the anode electrode may be irradiated with light having a wavelength of not more than 360 nanometers and a light intensity of not less than 5 $mW/cm^2$.

According to the second aspect, carbon dioxide reduction reaction on the cathode electrode is promoted by increasing the light intensity of the light condensed using the condenser. In other words, the production amount of the reduction product of carbon dioxide can be increased.

In the method for reducing carbon dioxide according to a third aspect of the present disclosure, the condenser may be a condensing lens or a condensing mirror in the first aspect.

According to the third aspect, light emitted from a general light source can be condensed in simple and efficient ways.

In the method for reducing carbon dioxide according to a fourth aspect of the present disclosure, the value of x may fall within the range of more than 0 and not more than 0.25 in the first aspect.

According to the fourth aspect, a wavelength region of the light absorbable by the $Al_xGa_{1-x}N$ layer is widened, and the light emitted from the general light source can be used efficiently.

In the method for reducing carbon dioxide according to a fifth aspect of the present disclosure, the GaN layer may be of n-type or $n^+$-type in the first aspect.

According to the fifth aspect, an electric resistance value of the GaN layer through which the electrons generated through photoexcitation migrate is lowered, and thereby the performance as a photochemical electrode used for reduction of carbon dioxide can be improved.

In the method for reducing carbon dioxide according to a sixth aspect of the present disclosure, at least a part of a surface of the $Al_xGa_{1-x}N$ layer may be covered with metal particles containing nickel or metal oxide particles containing nickel in the first aspect.

According to the sixth aspect, oxygen generation efficiency on the photochemical electrode can be improved due to co-catalytic action caused by the metal oxide containing nickel.

In the method for reducing carbon dioxide according to a seventh aspect of the present disclosure, the metal disposed on the surface of the cathode electrode may be indium, gold, or an alloy thereof in the first aspect.

According to the seventh aspect, carbon monoxide or formic acid can be generated efficiently as the reduction product of carbon dioxide.

In the method for reducing carbon dioxide according to an eighth aspect of the present disclosure, the first electrolyte may be a potassium hydrogen carbonate aqueous solution, a sodium hydrogen carbonate aqueous solution, a potassium chloride aqueous solution or a sodium chloride aqueous solution in the first aspect.

According to the eighth aspect, the electrolyte stored in the container can be used simply and is suitable as an electrolyte used for carbon dioxide reduction.

In the method for reducing carbon dioxide according to a ninth aspect of the present disclosure, the second electrolyte may be a sodium hydroxide aqueous solution or a potassium hydroxide aqueous solution in the first aspect.

According to the ninth aspect, the electrolyte stored in the container can be used simply and is suitable as an electrolyte used for carbon dioxide reduction.

In the method for reducing carbon dioxide according to a tenth aspect of the present disclosure, the carbon dioxide reduction device may be at room temperature and at atmospheric pressure in the step (b) of the first aspect.

According to the tenth aspect, carbon dioxide can be reduced without locating the carbon dioxide reduction device at special environment.

In the method for reducing carbon dioxide according to an eleventh aspect of the present disclosure, the light may be sunlight or pseudo sunlight in the step (b) of the first aspect.

According to the eleventh aspect, the carbon dioxide reduction reaction can be promoted by light energy outdoors or in an environment equivalent to the outdoors without using a special light source.

In the method for reducing carbon dioxide according to a twelfth aspect of the present disclosure, formic acid or carbon monoxide may be obtained in the step (b) of the first aspect.

According to the twelfth aspect, carbon dioxide is immobilized and various useful materials are obtained through the reduction reaction of carbon dioxide using the light energy.

Hereinafter, the method for reducing carbon dioxide according to the present disclosure will be described with reference to the drawings.

(Anode Electrode (Photochemical Electrode))

FIG. 1 is a cross-sectional view showing the anode electrode (i.e. photochemical electrode) according to the present disclosure. The anode electrode 10 shown in FIG. 1 comprises an $Al_xGa_{1-x}N$ layer 11 ($0<x\le 1$) to be irradiated with light, a GaN layer 12, an insulating substrate 13 used to form a nitride semiconductor layer (i.e., the $Al_xGa_{1-x}N$ layer 11 and the GaN layer 12), and a metal electrode 14 used to electrically connect to the anode electrode 10.

In a fabrication method of the anode electrode 10, generally, a nitride semiconductor layer is formed as a thin film on the insulating substrate 13. The fabrication method of the anode electrode 10 is not limited, as long as the thin film of the nitride semiconductor is formed on the insulating substrate 13. For example, the anode electrode 10 may be fabricated by an organometallic vapor-phase epitaxy method.

The materials of the insulating substrate 13 include, for example, a sapphire substrate or a silicon substrate. The materials of the insulating substrate 13 are not limited, as long as the nitride semiconductor thin film can be formed.

The metal electrode 14 is formed, for example, by a vacuum deposition method (e.g., resistive heating vapor deposition or electron-beam evaporation).

The basic function of the anode electrode 10 will be described below. The anode electrode 10 absorbs light at the region of the $Al_xGa_{1-x}N$ layer 11 to generate photoexcitation. The carriers (i.e., electrons and holes) generated through the photoexcitation contribute to oxidation-reduction reaction. In particular, the holes generated in the $Al_xGa_{1-x}N$ layer 11 migrate to the surface of the anode electrode 10. Then, the holes oxidize water in contact with the anode electrode 10 to generate oxygen. In other words, the anode electrode 10 functions as an oxygen generation electrode. On the other hand, the electrons generated through the photoexcitation are collected to the metal electrode 14 arranged in the anode electrode 10. Then, the electrons migrate to the cathode electrode through the conducting wire connected electrically.

Since the bandgap of the $Al_xGa_{1-x}N$ layer 11 is not less than 3.4 eV, the $Al_xGa_{1-x}N$ layer 11 is required to be irradiated with light having a wavelength of not more than 350 nanometers to use the $Al_xGa_{1-x}N$ layer 11 as the anode electrode 10 that utilizes light. For this reason, in light of effective use of the light, it is desirable that the value x which represents the composition ratio of aluminum contained in the $Al_xGa_{1-x}N$ layer 11 falls within the range $0<x\le 0.25$. Among others, it is desirable that the value x falls within the range $0<x\le 0.15$. The value x is not limited to this range, if the $Al_xGa_{1-x}N$ layer 11 can be irradiated with light having a wavelength of not less than the value of the bandgap of the $Al_xGa_{1-x}N$ layer 11.

When the $Al_xGa_{1-x}N$ layer 11 is irradiated with the light having a wavelength within the above wavelength range, the depth of the absorption is approximately 100 nanometers from the surface irradiated with the light. This depth may depend on the value of the bandgap of the $Al_xGa_{1-x}N$ layer 11. It is desirable that the $Al_xGa_{1-x}N$ layer 11 has a thickness of not less than 70 nanometers and not more than 1,000 nanometers. More desirably, the thickness is not less than 80 nanometers and not more than 200 nanometers.

In order to efficiently collect the electrons generated through light irradiation to the metal electrode 14, the $Al_xGa_{1-x}N$ layer 11 is stacked on the GaN layer 12. In order to lower the electric resistance of the GaN layer 12, it is desirable that the GaN layer 12 contains impurities. For example, the impurities are silicon.

Figure 2:
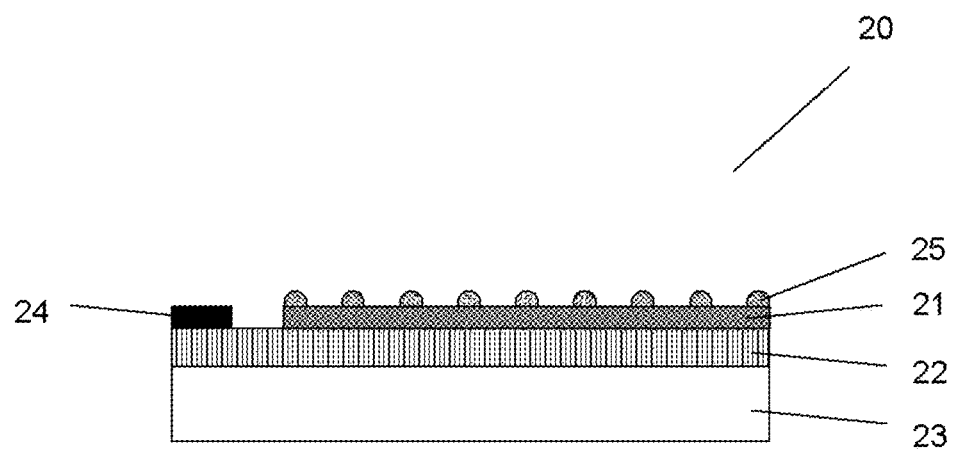
FIG. 2 is a cross-sectional view of another anode electrode according to the present disclosure.

In order to improve the oxygen generation efficiency and the durability of the anode electrode, as shown in FIG. 2, many metal particles containing nickel or many metal oxide particles containing nickel oxide may be dispersed on the surface of the $Al_xGa_{1-x}N$ layer 11. Each particle 25 has a diameter of not less than 100 nanometers and not more than a few micrometers. U.S. Pat. No. 8,414,758, which was filed by the present inventors, is incorporated herein by reference.

Figure 3:
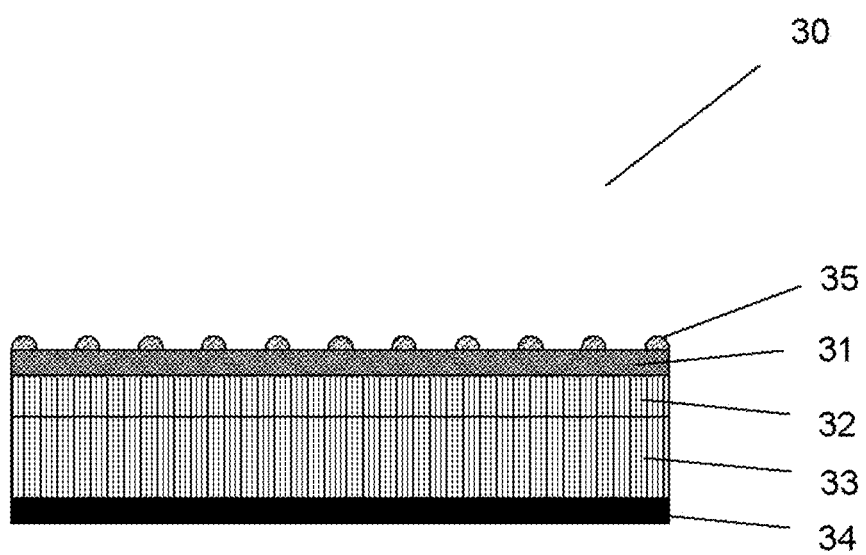
FIG. 3 is a cross-sectional view of still another anode electrode according to the present disclosure.

FIG. 3 is a cross-sectional view showing an anode electrode 30 in which a conductive substrate 33 is employed in place of the insulating substrate 13. As shown in FIG. 3, a GaN layer 32 and an $Al_xGa_{1-x}N$ layer 31 are formed in this order on the conductive substrate 33. In addition, a metal electrode 34 is formed on the opposite surface of the conductive substrate 33. For example, the conductive substrate 33 includes a single-crystal gallium nitride substrate or a gallium oxide substrate. In addition, the $Al_xGa_{1-x}N$ layer 31 and the GaN layer 32 have the same structure as the $Al_xGa_{1-x}N$ layer 11 and the GaN layer 12, respectively. In addition, nickel oxide particles 35 may be dispersed on the $Al_xGa_{1-x}N$ layer 31. The nickel oxide particle 35 has the same structure as the nickel oxide particle 25.

First Embodiment (Carbon Dioxide Reduction Device)

Figure 4:
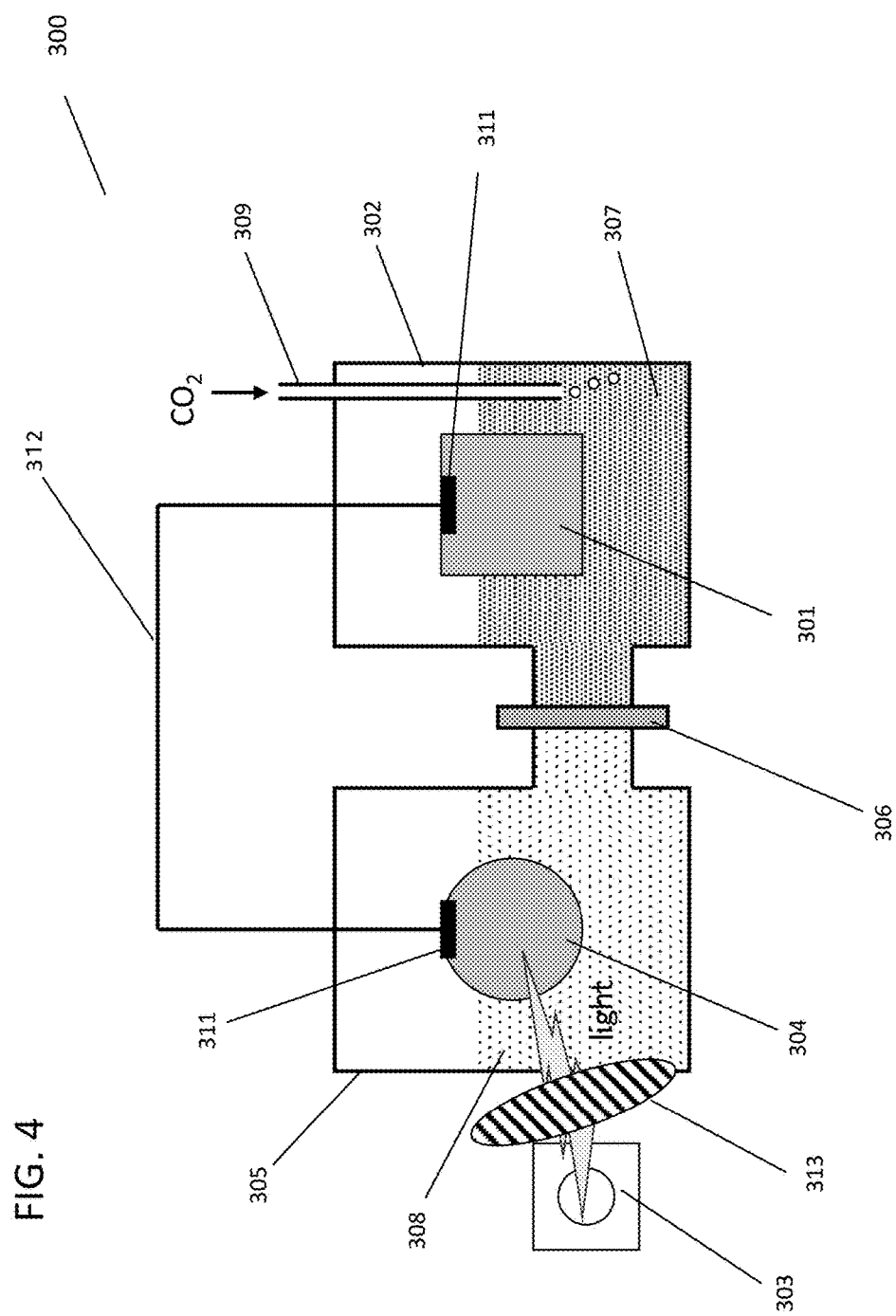
FIG. 4 is a schematic view of a carbon dioxide reduction device according to the present disclosure.

FIG. 4 is a schematic view showing a carbon dioxide reduction device 300. The carbon dioxide reduction device 300 has a cathode container 302, an anode container 305, a solid electrolyte membrane 306 and a condenser 313.

A first electrolyte 307 is stored in the cathode container 302. In addition, the cathode container 302 has a cathode electrode 301. The cathode electrode 301 is in contact with the first electrolyte 307. In particular, the cathode electrode 301 is immersed in the first electrolyte 307.

For example, the first electrolyte 307 is a potassium hydrogen carbonate aqueous solution, a sodium hydrogen carbonate aqueous solution, a potassium chloride aqueous solution or a sodium chloride aqueous solution. Furthermore, the first electrolyte 307 contains carbon dioxide. The concentration of the carbon dioxide is not limited. It is desirable that the first electrolyte 307 is acidic in a state where carbon dioxide is dissolved in the first electrolyte 307.

The material of the cathode electrode 301 on which carbon dioxide is reduced is a metal or a metal compound. It is desirable that the material of the cathode electrode 301 is gold, an alloy containing gold, or a gold compound, when carbon monoxide is generated. It is desirable that the material of the cathode electrode 301 is indium, an alloy containing indium, or an indium compound, when formic acid is generated.

The cathode electrode 301 may be composed of the predetermined metal only, however, may have a stacked structure of a substrate having a predetermined metal. For example, the cathode electrode 301 may be a plate in which the predetermined metal having a thin-film shape is formed on the conductive substrate such as glassy carbon, or a plate in which many metal particles are supported on the conductive substrate. At least a part of the cathode electrode 301 may be immersed in the first electrolyte 307.

A second electrolyte 308 is stored in the anode container 305. The anode container 305 includes an anode electrode 304. The anode electrode 304 is a photochemical electrode which functions by light irradiation.

Furthermore, the anode electrode 304 has a region formed of a nitride semiconductor in which the $Al_xGa_{1-x}N$ layer and the GaN layer are stacked. At least a part of the anode electrode 304 is in contact with the second electrolyte 308. In particular, the anode electrode 304 is immersed in the second electrolyte 308.

The first electrolyte 307 and the second electrolyte 308 may have the same solute, however, it is desirable that they have different solutes. For example, the second electrolyte 308 is a sodium hydroxide aqueous solution or a potassium hydroxide aqueous solution. It is desirable that the second electrolyte 308 has a concentration of not less than 1 mol/L. More desirably, the concentration is approximately 5 mol/L. It is desirable that the second electrolyte 308 is basic.

The solid electrolyte membrane 306 is interposed between the cathode container 302 and the anode container 305 to separate the first electrolyte 307 and the second electrolyte 308 from each other. In other words, in the carbon dioxide reduction device 300, the first electrolyte 307 and the second electrolyte 308 are not mixed with each other.

The solid electrolyte membrane 306 is not limited, as long as only protons travel through the solid electrolyte membrane 306 and other materials are prevented from travelling through the solid electrolyte membrane 306. For example, the solid electrolyte membrane 306 is Nafion.

The cathode electrode 301 and the anode electrode 304 comprise an electrode terminal 310 and an electrode terminal 311, respectively. These electrode terminals 310 and 311 are electrically and directly connected through a conducting wire 312. No external power supply such as a battery or a potentiostat is interposed between the electrode terminals 310 and 311.

As described later, the surface of the region of the anode electrode 304 immersed in the second electrolyte 308 is irradiated with light having a wavelength of not more than 350 nanometers from a light source 303 through the condenser 313. The condenser 313 is used to collect the light emitted from the light source to a certain region and has a structure to improve the light intensity per unit area. Since the light emitted from the light source 303 is collected through the condenser 313 in the carbon dioxide reduction device 300, the area on the anode electrode 304 irradiated with light is decreased, whereas the light intensity per unit area is increased. The condenser 313 is, for example, a condensing lens or a condensing mirror. The condenser 313 is not limited thereto, as long as the condenser 313 has a structure for improving the light intensity per unit area, compared to the light emitted from the light source 303. It is desirable that the condensing lens is formed of a material having a property that light having a wavelength of not more than 350 nanometers travels through the condensing lens. An example of the material having such a property is quartz or calcium fluoride. It is desirable that the condensing mirror is formed of a material having a property to reflect light having a wavelength of not more than 350 nanometers.

The carbon dioxide reduction device 300 can be used at room temperature and at atmospheric pressure.

(Carbon Dioxide Reduction Method)

Hereinafter, a method for reducing carbon dioxide using the carbon dioxide reduction device 300 will be described.

As shown in FIG. 4, the surface of the anode electrode 304 is irradiated with the light emitted from the light source 303 through the condenser 313. The light source 303 is, for example, a xenon lamp or a mercury lamp. In addition, sunlight or pseudo sunlight may be employed as the light source 303. The light emitted from the light source 303 has a wavelength of not more than 350 nanometers. It is desirable that the light emitted from the light source 303 has a wavelength of not less than 250 nanometers and not more than 325 nanometers.

Compared to a case where the anode electrode 304 is irradiated directly with the light source 303, in a case where the light is collected through the condenser 313, the irradiation area is decreased, whereas the light intensity per unit area is increased. In other words, compared to the case where no condenser 313 is used, the anode electrode 304 can be irradiated with the light having a higher light intensity. The collected light has an intensity of not less than 5 $mW/cm^2$ within a wavelength range of not more than 350 nanometers.

As shown in FIG. 4, it is desirable that the carbon dioxide reduction device 300 has a gas introduction pipe 309. Desirably, while carbon dioxide is supplied to the first electrolyte 307 through the gas introduction pipe 309, the carbon dioxide contained in the first electrolyte 307 is reduced. One end of the gas introduction pipe 309 is immersed in the first electrolyte 307. It is also desirable that, before starting the reduction of carbon dioxide, carbon dioxide is supplied to the first electrolyte 307 through the gas introduction pipe 309 so that a sufficient amount of carbon dioxide is dissolved in the first electrolyte 307.

When the cathode electrode 301 has a metal containing gold as a main component, carbon monoxide is selectively generated by reduction of the carbon dioxide contained in the first electrolyte 307. When the cathode electrode 301 has a metal containing indium as a main component, formic acid is selectively generated by reduction of the carbon dioxide contained in the first electrolyte 307.

EXAMPLES

The method for reducing carbon dioxide according to the present disclosure will be described in more detail with reference to the following examples.

Inventive Example 1

(Preparation of Anode Electrode)

A low-resistance monocrystalline gallium nitride substrate (thickness: 0.4 millimeters, surface area: 5 square centimeters) was used as a conductive substrate.

An n-type low-resistance GaN layer (thickness: 2.0 micrometers) doped with silicon (concentration: $2.5 \times 10^{18}$ $cm^{-3}$) and a non-doped $Al_xGa_{1-x}N$ layer (thickness: 100 nanometers, x=0.11, Al composition: 11%) were epitaxially grown on the conductive substrate by an organometallic vapor-phase epitaxy method.

Then, using a solution reaction, many nickel oxide particles (particle size: 100 nanometers—a few micrometers) were dispersed on the $Al_xGa_{1-x}N$ layer of the anode electrode.

Finally, a metal electrode (thickness: approximately 500 nanometers) formed of titanium (Ti)/aluminum (Al)/gold (Au) was formed on the opposite surface of the GaN substrate.

In this way, the anode electrode as shown in FIG. 3 was obtained.

(Assembling of Carbon Dioxide Reduction Device)

A carbon dioxide reduction device as shown in FIG. 4 was assembled using the anode electrode. The distance between the anode electrode and the cathode electrode was approximately 8 centimeters. The details of the carbon dioxide reduction device will be described below.

Cathode electrode: Gold plate (thickness: 0.5 millimeters, surface area: 4 square centimeters)

First electrolyte: Potassium chloride aqueous solution having a concentration of 3.0 mol/L (volume: 180 milliliters)

Second electrolyte: Sodium hydroxide aqueous solution having a concentration of 5.0 mol/L (volume: 180 milliliters)

Solid electrolyte membrane: Nafion film (available from DuPont, Nafion 117)

Light source: Xenon lamp (output: 300 W)

Condenser: Condensing lens (condensing magnification ratio: 10 times)

A carbon dioxide gas was supplied through a gas introduction pipe to the first electrolyte for thirty minutes.

The light emitted from the light source had a wavelength of not more than 350 nanometers. When the condenser was not used, the light intensity thereof was 1.75 mW/cm$^2$ (irradiation area: 10 square centimeters). On the other hand, when the condenser was used, the light intensity thereof was 17.5 mW/cm$^2$ (irradiation area: 1 square centimeter).

The anode container comprised a window (not shown). The surface of the anode electrode was irradiated with the light condensed through the condenser for a certain time through the window.

Comparative Example 1

An experiment similar to the inventive example 1 was conducted, except that the condenser was not used. In other words, the total value of the light energy emitted from the light source was the same as that of the inventive example 1, however, the light intensity per unit area on the anode electrode was one tenth as large as that of the inventive example 1 (that is, the irradiation area was ten times as large as that of the inventive example 1).

(Reduction of Carbon Dioxide)

In both cases of the inventive example 1 and the comparative example 1, when the surface of the anode electrode was irradiated with the light, it was observed that the reaction electric current flowed through the conducting wire. On the other hand, when the irradiation with the light was interrupted, it was observed that the reaction electric current did not flow through the conducting wire. This means that some sort of reaction was generated on the anode electrode and the cathode electrode by the irradiation with light.

The reaction electric current amount of the comparative example 1 is substantially the same as that of the inventive example 1. This means that the reaction electric current amount per unit area in the inventive example 1 is approximately ten times as large as that of the comparative example 1.

The present inventors researched how the carbon dioxide was reduced in more detail as below. In particular, in the state where the cathode container was hermetically sealed, that is, in the state where carbon dioxide did not leak from the cathode container, the anode electrode according to the inventive example 1 was irradiated with light. Due to this irradiation with light, carbon dioxide was reduced in the cathode container. The kind and amount of the gaseous reaction product generated through the reduction of carbon dioxide were analyzed by a gas chromatography method. Similarly, the kind and amount of the liquid reaction product were analyzed by a liquid chromatography method or a headspace gas chromatography.

Furthermore, generation efficiency (i.e., Faraday efficiency) of the reaction product was calculated on the basis of the integrated value of the reaction electric current amount obtained by irradiating the surface of the anode electrode with light. The generation efficiency (i.e., Faraday efficiency) means a ratio of the reaction charge amount used for the generation of the reaction product to the total charge amount generated by light irradiation. In other words, the following mathematical formula is satisfied.

(Generation efficiency)=(Reaction charge amount used for the generation of the reactant)/(Total charge amount)×100(%)

Table 1 shows the generation efficiency (i.e., Faraday efficiency) of the reaction product obtained in the inventive example 1 and the comparative example 1.

TABLE 1

|  | Hydrogen [%] | Carbon monoxide [%] | Formic acid [%] |
|---|---|---|---|
| Inventive example 1 | 8.63 | 80.1 | 2.17 |
| Comparative example 1 | 36.2 | 34.8 | 6.28 |

In the inventive example 1, it was observed that some hydrogen was generated, however, the main product was carbon monoxide, and that the reduction reaction of carbon dioxide occurred efficiently. Furthermore, oxygen was generated in the anode container through oxidation reaction of water. The amount of the oxygen generated in the anode container corresponded to the amount of the reaction product generated in the cathode container. In other words, it was observed that a catalytic reaction in which carbon dioxide was reduced on the cathode electrode occurred due to irradiation of the anode electrode with light and that carbon dioxide was converted into carbon monoxide efficiently.

On the other hand, similarly to the case of the inventive example 1, the reduction reaction of carbon dioxide occurred on the cathode electrode in the comparative example 1, however, hydrogen was generated significantly, and the amount of the generated carbon monoxide was less than half that of the inventive example 1.

From the above results, it was observed that the generation efficiency of reduction product of carbon dioxide is increased from 41.1% (see the comparative example 1) to 82.7% (see the inventive example 1) by using the carbon dioxide reduction device comprising the condenser, although the total amount of the light energy given by the light source is not varied. Furthermore, it was observed that the selectively of carbon monoxide which is a main product (i.e., ratio of the generation efficiency of the focused product to the generation efficiency of the total products) is also increased from 45.0% (see the comparative example 1) to 88.1% (see the inventive example 1). The present inventors considered that this is because the intensity of the light with which the anode electrode was irradiated (i.e., the light intensity per unit area) was increased by the condenser.

A gold plate was used as the cathode electrode in the inventive example 1 and the comparative example 1. A similar result was obtained in a case using a glassy carbon substrate on which gold particles were supported.

A similar result was also obtained in a case using the anode electrode shown in FIG. 2 (substrate: a sapphire substrate).

Inventive Example 2

An experiment similar to the inventive example 1 was conducted, except that the condensing magnification ratio of the condenser was variable. In other words, the reduction experiment of carbon dioxide was conducted, while the intensity per unit area of the light with which the anode electrode was irradiated was varied.

Figure 5:
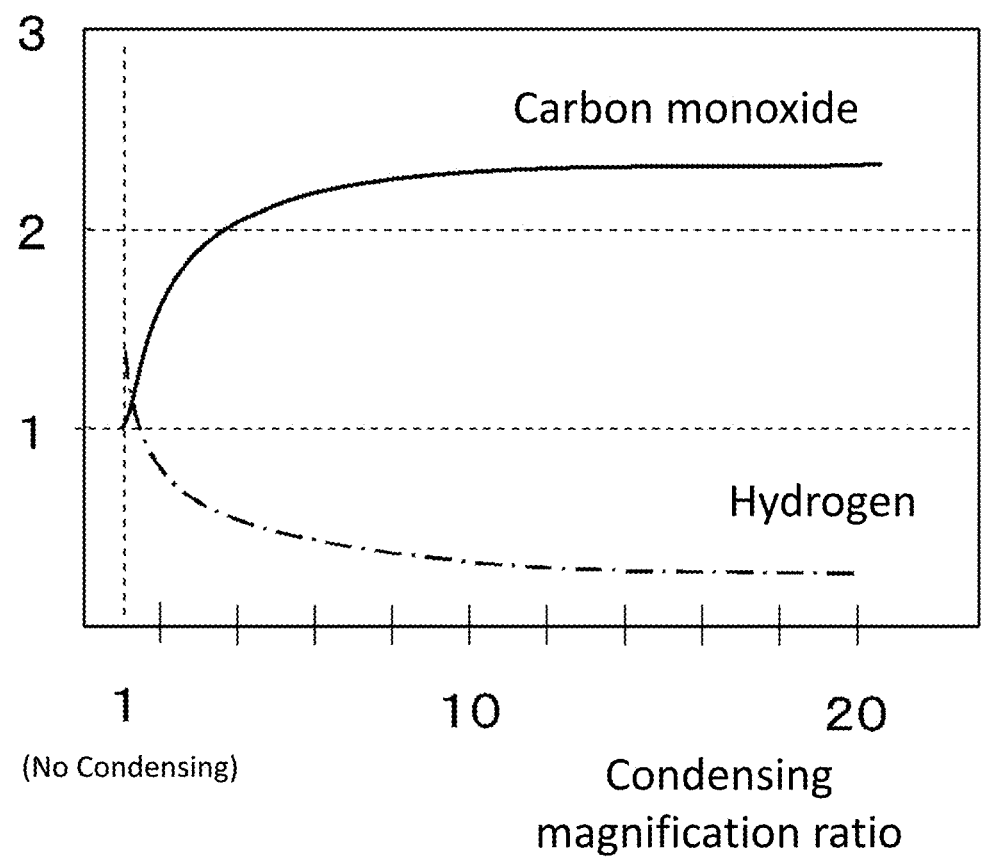
FIG. 5 is a graph showing a result of an inventive example 2.

FIG. 5 shows the result of the inventive example 2. The horizontal axis represents the magnification ratio of the condenser. The vertical axis represents the production amount of carbon monoxide and hydrogen. When the carbon dioxide reduction device according to the present disclosure was used, carbon monoxide and hydrogen were produced as the reduction product of carbon dioxide. As shown in FIG. 5, the production amount of hydrogen was decreased with an increase in the condensing magnification ratio. On the other hand, the production amount of carbon monoxide was increased with an increase in the condensing magnification ratio.

The production amount of carbon monoxide in a state where the condenser had approximately three times the condensing magnification ratio (light intensity: approximately 5 mW/cm$^2$) was approximately twice as many as the production amount of carbon monoxide in a state where the condenser had one time the condensing magnification ratio (light intensity: approximately 1.75 mW/cm$^2$). Also in a case where the condensing magnification ratio was increased, the production amount of carbon monoxide continued to be mildly increased. On the other hand, the production amount of hydrogen was rapidly decreased until the condensing magnification ratio of the condenser was increased to approximately three times. While the condensing magnification ratio was increased in the range of over three times, the production amount of hydrogen was mildly decreased. In other words, the production amount of carbon monoxide was rapidly increased in a state where the condensing magnification ratio was not less than one time and not more than three times (i.e., light intensity: not less than 1.75 mW/cm$^2$ and not more than 5 mW/cm$^2$); whereas the production amount of carbon monoxide was mildly increased in a state where the condensing magnification ratio was not less than three times (i.e., light intensity: not less than 5 mW/cm$^2$).

Inventive Example 3

An experiment similar to the inventive example 1 was conducted, except that a pseudo sunlight source having an air mass (AM) of 1.5 was used.

As a result, it was observed that a reaction production amount of carbon dioxide is increased by arranging the condenser also in a case where the light source itself is replaced. In addition, a similar result was obtained also in a case where sunlight was used as the light source.

Inventive Example 4

An experiment similar to the inventive example 1 was conducted, except that an indium plate (surface area: 18 square centimeters) and a potassium hydrogen carbonate aqueous solution (volume: 180 milliliters) having a concentration of 0.5 mol/L were used as the cathode electrode and the first electrolyte, respectively.

Comparative Example 2

An experiment similar to the inventive example 4 was conducted, except that the condenser was not used. In other words, the total amount of the light energy emitted by the light source was the same; however, the light intensity per unit area on the surface of the anode electrode was one tenth as large as that of the inventive example 4.

Table 2 shows generation efficiency (i.e., Faraday efficiency) of the reaction product obtained in the inventive example 4 and the comparative example 2.

TABLE 2

|  | Hydrogen [%] | Carbon monoxide [%] | Formic acid [%] |
|---|---|---|---|
| Inventive example 4 | 5.55 | 17.3 | 73.3 |
| Comparative example 2 | 6.66 | 28.5 | 47.8 |

As shown in Table 2, when an indium plate was used as the cathode electrode, generation efficiency of the reduction product material of carbon dioxide was increased from 76.3% (see the comparative example 2) to 90.6% (see the inventive example 4) by using the condenser. Furthermore, the selectivity of formic acid which is a main product material was increased from 57.6% (see the comparative example 2) to 76.2% (see the inventive example 4).

The indium plate was used as the cathode electrode in the inventive example 4. A similar result was obtained in a case using a glassy carbon substrate on which indium particles were supported.

As just described, by using the carbon dioxide reduction device having a condenser according to the present disclosure, the reduction efficiency of carbon dioxide is improved and the amount of the reaction product generated from carbon dioxide is increased.

INDUSTRIAL APPLICABILITY

The present invention provides a carbon dioxide reduction device used to reduce carbon dioxide using light energy. The present invention also provides a method for reducing carbon dioxide using the carbon dioxide reduction device.

REFERENTIAL SIGNS LIST 11, 21, 31 Al$_x$Ga$_{1-x}$N layer
12, 22, 32 GaN layer
13, 23 Insulating substrate
33 Conductive substrate
14, 24, 34 Metal electrode
25, 35 Nickel oxide particle
301 Cathode electrode
302 Cathode container
303 Light source
10, 30, 304 Anode electrode
305 Anode container
306 Solid electrolyte membrane
307 First electrolyte
308 Second electrolyte
309 Gas introduction pipe
310, 311 Electrode terminal
312 Conducting wire
313 Condenser

The invention claimed is:
1. A method for reducing carbon dioxide using a carbon dioxide reduction device, the method comprising:
(a) preparing the carbon dioxide reduction device comprising:
a cathode container;
an anode container;
a solid electrolyte membrane;

a condenser;

a cathode electrode; and an anode electrode, wherein the cathode electrode comprises a metal or a metal compound on a surface thereof;

the anode electrode comprises, on a surface thereof, a region formed of a nitride semiconductor layer in which a GaN layer and an $Al_xGa_{1-x}N$ layer ($0<x\leq1$) are stacked;

a first electrolyte is stored in the cathode container;

a second electrolyte is stored in the anode container;

the cathode electrode is in contact with the first electrolyte;

the anode electrode is in contact with the second electrolyte;

the solid electrolyte membrane is interposed between the cathode container and the anode container;

the first electrolyte contains carbon dioxide; and the cathode electrode is electrically connected to the anode electrode without an external power supply; and (b) irradiating the anode electrode with light condensed through the condenser and having a wavelength of not more than 360 nanometers to reduce the carbon dioxide contained in the first electrolyte on the cathode electrode.

2. The method according to claim 1, wherein in the step (b), the light with which the anode electrode is irradiated has a light intensity of not less than 5 $mW/cm^2$.

3. The method according to claim 2, wherein the condenser is a condensing lens or a condensing mirror.

4. The method according to claim 1, wherein the value of x falls within the range of more than 0 and not more than 0.25.

5. The method according to claim 1, wherein the GaN layer is of n-type or $n^+$-type.

6. The method according to claim 1, wherein at least a part of a surface of the $Al_xGa_{1-x}N$ layer is covered with metal particles containing nickel or metal oxide particles containing nickel.

7. The method according to claim 1, wherein the metal disposed on the surface of the cathode electrode is indium, gold, or an alloy thereof.

8. The method according to claim 1, wherein the first electrolyte is a potassium hydrogen carbonate aqueous solution, a sodium hydrogen carbonate aqueous solution, a potassium chloride aqueous solution or a sodium chloride aqueous solution.

9. The method according to claim 1, wherein the second electrolyte is a sodium hydroxide aqueous solution or a potassium hydroxide aqueous solution.

10. The method according to claim 1, wherein the carbon dioxide reduction device is at room temperature and at atmospheric pressure in the step (b).

11. The method according to claim 1, wherein the light is sunlight or pseudo sunlight in the step (b).

12. The method according to claim 1, wherein formic acid or carbon monoxide is obtained in the step (b).

* * * * *